United States Patent
Bracci et al.

(10) Patent No.: US 8,440,794 B2
(45) Date of Patent: May 14, 2013

(54) PEPTIDE SEQUENCES, THEIR BRANCHED FORM AND USE THEREOF FOR ANTIMICROBIAL APPLICATIONS

(75) Inventors: Luisa Bracci, Siena (IT); Chiara Falciani, Siena (IT); Alessandro Pini, Siena (IT)

(73) Assignee: Universita' Degli Studi di Siena, Siena (IT)

( * ) Notice: Subject to any disclaimer, the term of this patent is extended or adjusted under 35 U.S.C. 154(b) by 0 days.

(21) Appl. No.: 13/122,426

(22) PCT Filed: Oct. 5, 2009

(86) PCT No.: PCT/IB2009/054347
§ 371 (c)(1),
(2), (4) Date: Apr. 4, 2011

(87) PCT Pub. No.: WO2010/038220
PCT Pub. Date: Apr. 8, 2010

(65) Prior Publication Data
US 2011/0190198 A1 Aug. 4, 2011

Related U.S. Application Data

(60) Provisional application No. 61/102,854, filed on Oct. 5, 2008.

(51) Int. Cl.
*A61K 38/08* (2006.01)
*C07K 7/06* (2006.01)
*A61P 31/04* (2006.01)

(52) U.S. Cl.
USPC ........................................... 530/328; 514/2.4

(58) Field of Classification Search ....................... None
See application file for complete search history.

(56) References Cited

FOREIGN PATENT DOCUMENTS
WO 2006/006195 1/2006

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BloL (2002) 324, 373-386.*
Pini et al., "Antimicrobial Activity of Novel Dendrimeric Peptides Obtained by Phage Display Selection and Rational Modification" Antimicrobial Agents and Chemotherapy, vol. 49, No. 7, Jun. 27, 2005, pp. 2665-2672.
Pini et al., "Branched peptides as therapeutics" Current Protein and Peptide Science, vol. 9, No. 5, Oct. 1, 2008, pp. 468-477.

* cited by examiner

*Primary Examiner* — Julie Ha
*Assistant Examiner* — Li Ni Komatsu
(74) *Attorney, Agent, or Firm* — Lucas & Mercanti, LLP

(57) ABSTRACT

The present invention relates to an antibacterial peptide having from the amino to the carboxylic terminal an amino acid sequences selected from the group of: KKIRVRLSA, SEQ ID NO. 1, RRIRVRLSA, SEQ ID NO. 2, KRIRVRLSA, SEQ ID NO. 3, RKIRVRLSA, SEQ ID NO. 4 or a derivative thereof and uses thereof.

18 Claims, 4 Drawing Sheets

Figure 1:
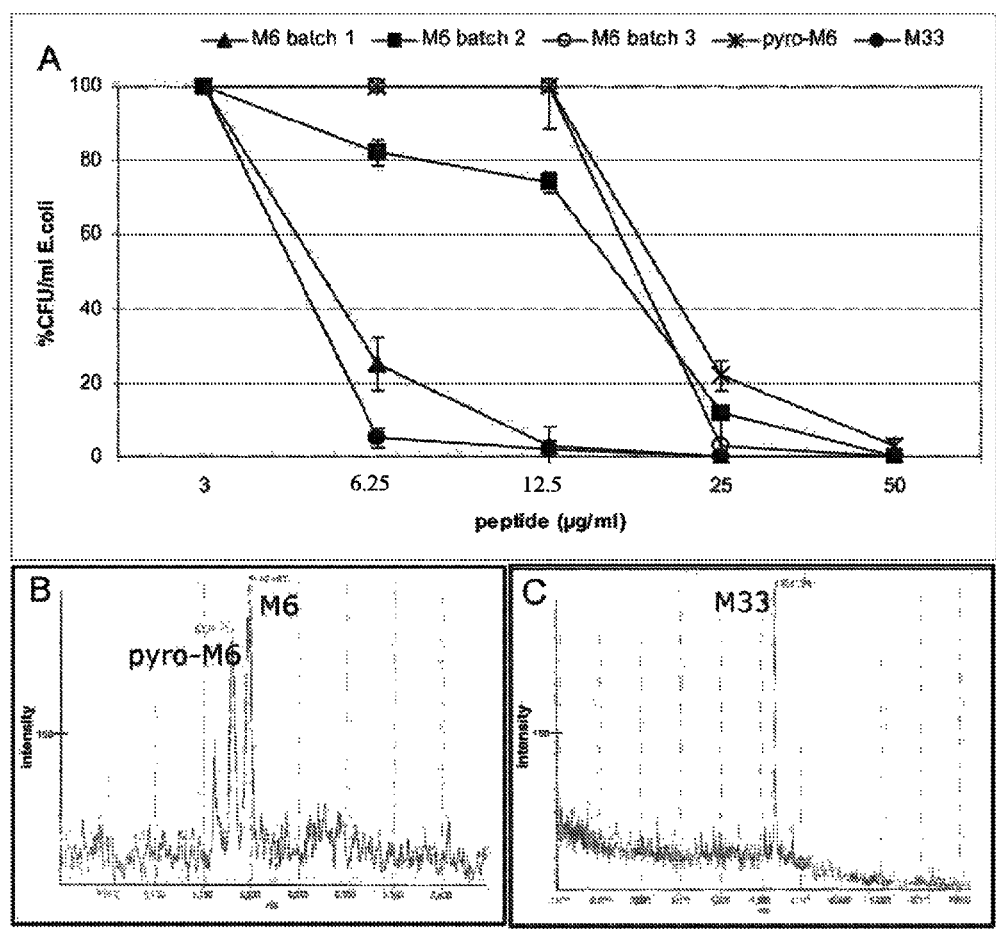

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Lys Lys Ile Arg Val Arg Leu Ser Ala
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Arg Arg Ile Arg Val Arg Leu Ser Ala
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Lys Arg Ile Arg Val Arg Leu Ser Ala
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide
```

```
-continued

<400> SEQUENCE: 4

Arg Lys Ile Arg Val Arg Leu Ser Ala
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Gln Lys Lys Ile Arg Val Arg Leu Ser Ala
1               5                   10
```

PEPTIDE SEQUENCES, THEIR BRANCHED FORM AND USE THEREOF FOR ANTIMICROBIAL APPLICATIONS

This application is a U.S. national stage of PCT/IB2009/054347 filed on Oct. 5, 2009 which claims priority to and the benefit of U.S. Provisional Application No. 61/102,854 filed on Oct. 5, 2008, the contents of which are incorporated herein by reference.

TECHNICAL FIELD OF THE INVENTION

The instant invention refers to the identification of potent antimicrobial peptide sequences that are particularly resistant to protease activity and, consequently, very suitable for in vivo use, in particular when synthesized in the tetra-branched MAP form. The sequences of the present invention (KKIRVRLSA, SEQ ID No. 1, RRIRVRLSA, SEQ ID No. 2, KRIRVRLSA, SEQ ID No. 3, RKIRVRLSA, SEQ ID No. 4) derived from the previously reported peptide M6 that brought a Gln as first amino-terminal residue. Elimination of the Gln gave an unforeseen and surprising improvement in peptide stability and lot to lot homogeneity and, consequently allowed a reliable method for peptide synthesis that is particularly difficult for the M6 peptide.

BACKGROUND ART

The growing emergency of multi-drug resistant-bacteria is a global concern, mostly in those countries where antibiotics are widely used in clinics. A number of pathogens like *Staphylococcus aureus, Mycobacterium tuberculosis*, some enterococci, *Pseudomonas aeruginosa* and many other Gram-negative bacteria have developed resistance against most traditional antibiotics as well as against those of new generation (Wenzel and Edmond 2000). It has therefore become increasingly important to develop new antibiotics. This demand urges the community of researchers and the pharmaceutical companies to consider new antimicrobial agents. Antimicrobial peptides are considered one of the best alternative to traditional antibiotics which generally cause the selection of resistant bacteria (Hancock and Sahl 2006). Most antibacterial peptides are components of the innate immunity of animals, including humans, plants and fungi (Zasloff, 2002). They usually consist of 6-50 amino acid residues and have a positive net charge. Cationic peptides interact selectively with anionic bacterial membranes and with other negatively charged structures such as LPS and DNA. Eukaryotic membranes, in their external layer, are normally less negatively charged than bacteria's, and, differently from bacterial membrane, they are also stabilized by cholesterol molecules. These differences are the basis of cationic peptides' specificity. The mechanism of action of cationic antimicrobial peptides is consequently due to their specific binding to bacterial membranes, which provokes cell permeation and, in some cases, metabolic pathways inhibition.

Many studies then, aimed to the identification and characterization of antimicrobial peptide sequences by studying their mechanism of action, their toxicity for eukaryotic cells and their therapeutic efficacy when administered topically or systemically. Unfortunately, two main problems hindered the development of antimicrobial peptide drugs so far. The first is that selectivity of natural antimicrobial peptides for bacteria is generally too low and they appear to be very toxic for eukaryotic cells, particularly erythrocytes, generating a high level of haemolysis. The second is linked to the generally short half-life of peptides in vivo. These are the main reasons for which only few cationic peptides reached the market in the last 10 years (polymyxin and daptomycin are two successful examples).

A few years ago, researchers began to concentrate on the identification of novel peptide sequences of non-natural origin, selected in the laboratory by rational design or screening of combinatorial libraries. The aim was to find peptides with better biological properties in terms of general toxicity and specificity for bacteria and improved half-life for drug development.

In the inventors' laboratory, a non-natural peptide sequence was identified, which showed a strong antimicrobial activity especially against Gram-negative bacteria (Pini et al, 2005). The peptide, (QKKIRVRLSA, SEQ ID No. 5, called M6) was obtained by rational modifications of a sequence identified from a combinatorial library, was synthesized in the MAP tetra-branched form where four identical peptide sequences are linked together by a lysine core. This molecule showed a high resistance to proteases and peptidases therefore overcoming the problem of short half-life (Bracci et al., 2003; Falciani et al., 2007). The branched antimicrobial peptide M6 has already been characterized for its biological activity against a number of bacteria, including several multi drug resistant clinical isolates, for its interactions with DNA, for its in vitro toxicity against several eukaryotic cell lines, as well as for its haemolytic activity, for its immunogenicity, for its in vivo toxicity when injected intraperitoneally or intravenously (Pini et al, 2007).

During all experiments carried out for M6 characterization we noted that different synthesis of M6 produced peptides with non homogeneus activities (batch to batch dissimilarity) (FIG. 1A). Mass spectrometry analysis revealed that the first aminoacid of M6, namely Gln, converts to pyroglutamic acid (FIG. 1B). The presence of the different peptide containing pyroglutramic acid and not Gln changes from batch to batch in an unpredictable percentage. The complete elimination of this secondary product is in facts impossible, firstly, because it is not easily discarded during HPLC purification because of the similar retention time with the main product, and secondly because it is continuously produced from the parent peptide when in solution. Since the pyroGlu-analogue showed a sensibly reduced antimicrobial activity with respect to the Gln analogue, the overall activity of the mixture varied from batch to batch (FIG. 1A).

In order to minimize batch to batch dissimilarity, in the perspective of a large scale peptide production for preclinical experiments and, possibly, for industrial manufacturing, we eliminated the first Gln residue from M6 and also replaced the first two Lys with Arg or alternated the first two residues with Lys and Arg. This produced the following 9-mer sequences deprived of the first Gln present in M6 sequence: KKIRVRLSA, SEQ ID NO. 1, called M33; RRIRVRLSA, SEQ ID NO. 2, called M34; KRIRVRLSA, SEQ ID NO. 3, called M35; RKIRVRLSA, SEQ ID NO. 4, called M36. These sequences are the object of the present application.

The new peptides were subjected to several characterizations described in the examples below.

Practically, the elimination of a single amino acid residue at the N-terminal end of M6 peptide sequence, and the possible alternation of Lys and Arg in the first two positions, produces a better antimicrobial activity, and does not cause any different behaviour in terms of side-toxicity and mechanism of action. Indeed, it produces a strong improvement in the synthesis liability, rendering the sequences of peptides M33, M34, M35 and M36 much more suitable for an industrial development with respect to M6. M33, M34, M35 and M36 sequences, thanks to the improved stability and batch to batch homogeneity, are ideal candidates for the development of antimicrobial drugs.

DESCRIPTION OF INVENTION

It is an object of the present invention the peptide sequences KKIRVRLSA, SEQ ID NO. 1, M33, RRIRVRLSA, SEQ ID NO. 2, M34, KRIRVRLSA, SEQ ID NO. 3, M35, RKIRVRLSA, SEQ ID NO. 4, M36, synthesized in monomeric or dendrimeric structure, preferably in the Multiple Antigen Peptide (MAP) form that follows the general formula:

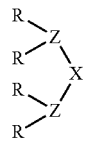

where R is a monomeric peptide with sequence chosen in the group of M33, M34, M35 and M36 (all R are the same sequence in one MAP molecule), X is a tri-functional molecule and Z is a tri-functional molecule as X or the following chemical group:

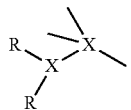

where R and X are defined above.

It is a further object of the invention an antibacterial peptide having from the amino to the carboxylic terminal an amino acid sequences selected from the group of: KKIRVRLSA, SEQ ID NO. 1, RRIRVRLSA, SEQ ID NO. 2, KKIRVRLSA, SEQ ID NO. 3, RKIRVRLSA, SEQ ID NO. 4 or a derivative thereof, wherein one amino acid residue is replaced by an alanine residue or wherein one positively charged amino acid is replaced by another positively charged amino acid. Preferably the peptide is of linear form. More preferably the peptide is multimerised on a skeleton of polyacrylamide, on a skeleton of dextrane units or on a skeleton of ethylene glycol units. Still preferably the peptide is in the form of Multiple Antigenic Peptides (MAP), having the following formula:

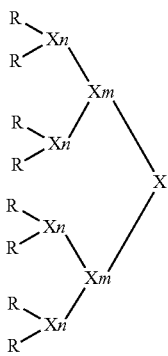

in which R is the peptide as claimed in claim 1; X is a trifunctional molecule; m=0 or 1; n=0 or 1; when m and n are 0 the peptide is a dimer; when m=1 and n=0 the peptide is a tetramer, when m=1 and n=1 the peptide is an octamer.

Preferably X is a trifunctional unit. More preferably the trifunctional unit comprises at least two functional aminic groups. Still preferably X is lysine, ornithine, nor-lysine or amino alanine. Yet preferably X is aspartic acid or glutamic acid. More preferably, X is propylene glycol, succinic acid, diisocyanates or diamines derivative.

It is a further object of the invention the peptide as described above for medical use. Preferably as an antibacterial drug.

It is a further object of the invention a pharmaceutical composition comprising a pharmaceutically acceptable and effective quantity of the peptide as described above. Preferably the composition is in the form of a solution to be injected in individuals for systemic use, more preferably in the form of a solution to be injected as detoxifying agent for LPS neutralization, still preferably in the form of eyewash, mouth wash, ointment, or solution for topic use.

It is a further object of the invention a disinfectant and/or detergent preparation with antibacterial activity comprising the peptide of the invention.

It is also an object of the invention the use of the peptide of the invention as a preservative for the preparation of food products and/or of cosmetic products and/or of homeopathic products.

It is object of the present invention the use of such peptides as antimicrobial agents for medical, veterinary and agronomic applications.

The present invention sequences are advantageous in respect to the already described M6 peptide because of their stability and strong batch to batch homogeneity in terms of both molecular composition and biological activity. M6 sequence (QKKIRVRLSA, SEQ ID NO. 5) included a Gln aminoacid as the first N-terminal residue. This aminoacid tended to convert spontaneously to pyro-glutamic acid in an unpredictable amount, The presence of pyro-glutamic acid in the batch caused a sensible decrease in the overall peptide activity depending on the percentage of the pyro-glutamic acid (FIG. 1A). In facts M6 peptide antimicrobial activity is not consistent in the long term and this affects negatively manufacturing scale up. The simple, and only apparently trivial, elimination of first Gln from M6 sequence, and, possibly the alternation of the first two residues with Lys and Arg, produced new peptide sequences with a strongly improved stability and batch to batch homogeneity, making the large scale manufacture reliable. This crucial feature along with its very encouraging antimicrobial activity makes peptides M33, M34, M35 and M36 optimal candidates for the development of new antibacterial drugs.

The invention will be now described by non limiting examples referring to the following figures:

FIG. 1. A, Antibacterial activity against *E. coli* TG1 cells. Comparison of the following tetra-branched peptides: M6 batch 1 synthesis (triangles), M6 batch 2 synthesis (squares), M6 batch 3 synthesis (white circles), which contain a mixture of Gln and pyroGlu (in unknown percentages) as first amino-acid, gyro-M6 (asterisks), where the first amino-acid is 100% pyroGlu, and M33 (black circles), in which the first Gln was deleted. Peptide containing 100% pyroGlu gave the worst result confirming that modification of Gln into pyroGlu decreased antibacterial activity. M6 peptides containing both Gln and pyroGlu showed intermediate antimicrobial activities. Elimination of the first residue from the M6 sequence improved peptide activity as demonstrated by the curve for M33. SD derived by means of three different experiments. Many different syntheses of M33 (and also of M34, M35 and M36, here not shown) gave perfectly overlapping results without any wavering outcome. B, Mass spectrometry analysis of tetra-branched peptide M6 crude mixture. Calculated molecular mass of M6 was 5195 Da. Two main peaks are present, one at 5197 Da corresponding to unmodified M6 and one at 5179 Da that corresponds to the secondary product with one pyroGlu in first position in the place of one of the four Gln. C, Mass spectrometry analysis of tetrabranched peptide M33 after 24 hours of incubation in serum. The peptide appears as a single peak at the expected molecular mass (4683 Da).

Figure 2:
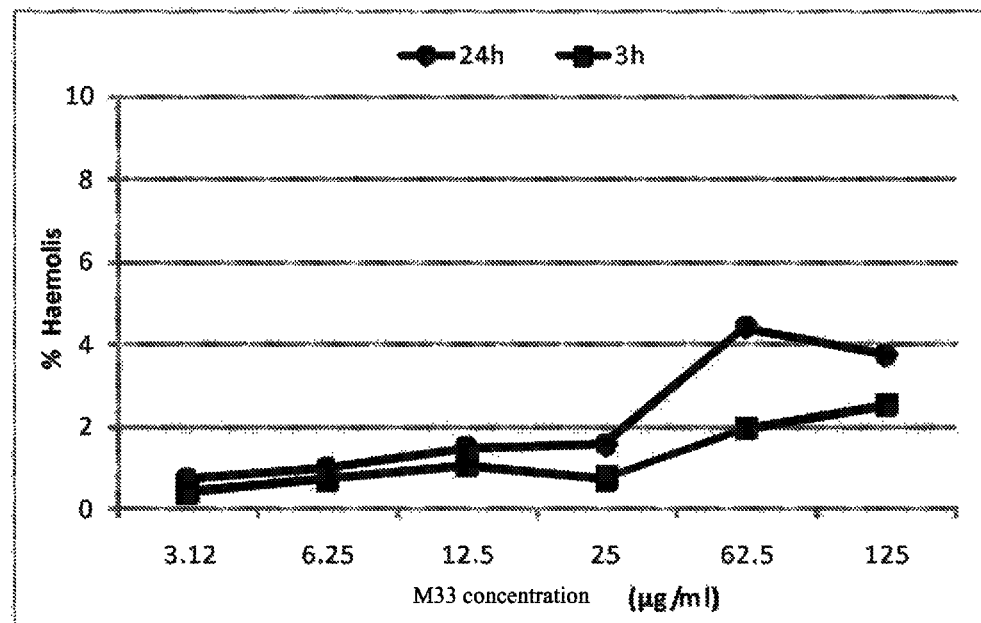

FIG. 2. Percentage of haemolysis provoked by tetra-branched M33 peptide incubated 3 or 24 hours with human red blood cells. At the highest concentration it caused only negligible haemolytic activity.

Figure 3:
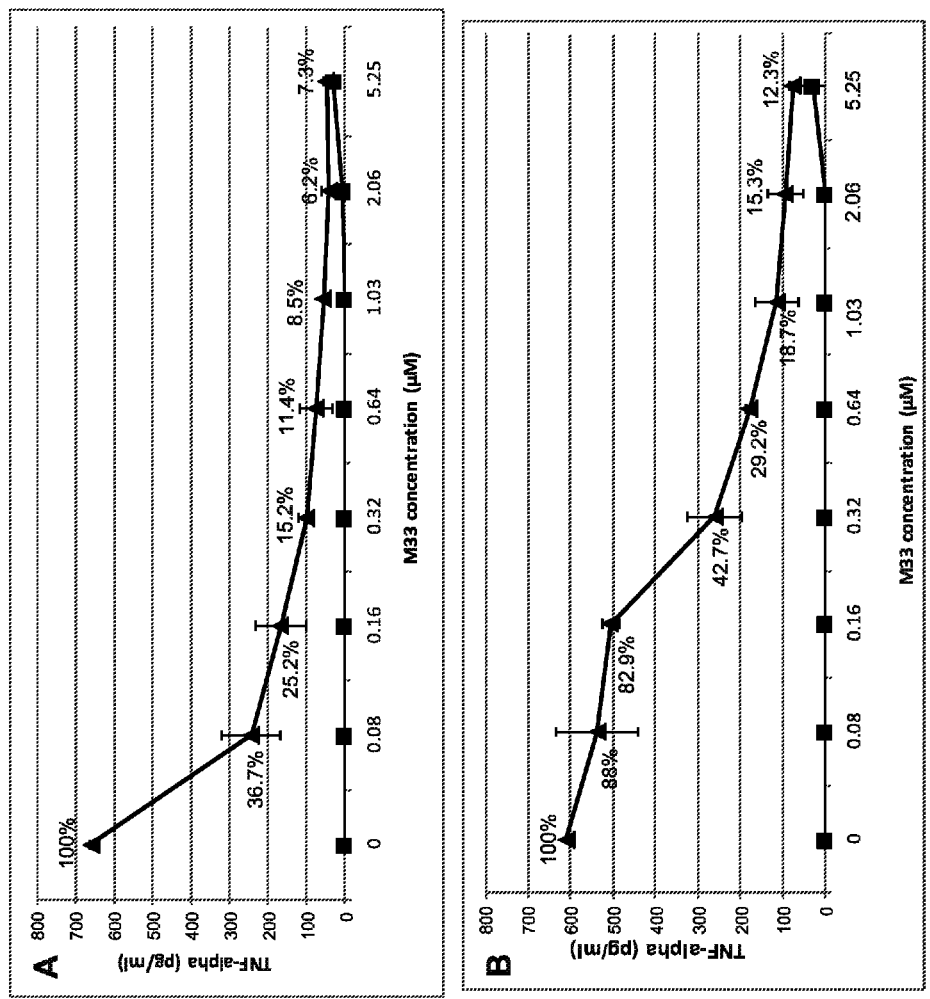

FIG. 3. Inhibition of TNF-α release by neutralization of LPS. A, Raw 264.7 cells were incubated with LPS from *P. aeruginosa* 20 ng/ml and M33. Triangles indicate incubation with LPS and different concentrations of M33. Squares indicate incubation with M33 only. B, Raw 264.7 cells were incubated with LPS from *K. pneumoniae* 5 ng/ml and M33. Triangles indicate incubation of macrophages with LPS and different concentrations of M33. Squares indicate incubation of macrophages with M33 only. SD derived by means of three different experiments. 100% indicates the maximum amount of TNF-α produced by macrophages when incubated with LPS without M33. The other percentages indicate the amount of TNF-α produced by macrophages when incubated with LPS and M33, with respect to 100%. Basal levels of TNF-α were negligible. MIC of M33 is indicated by the arrow.

Figure 4:
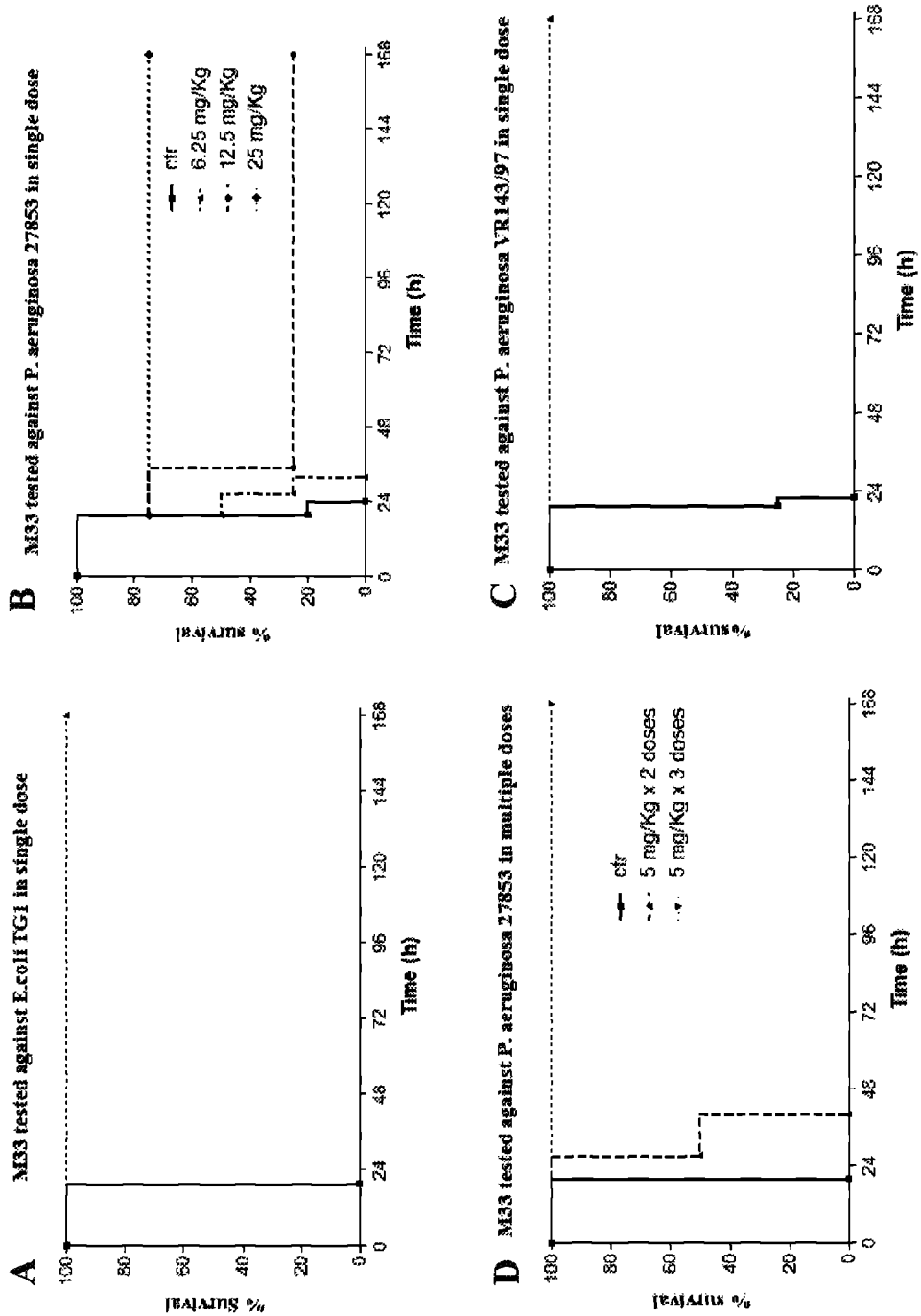

FIG. 4. In vivo antibacterial activity of tetra-branched M33 peptide. A, Balb-c mice (20 g) were intra-peritoneally injected with a lethal amount of *E. coli* TG1 cells ($1.5 \times 10^9$ CFU). Continuous line (Ctr) indicates mice only injected ip with bacteria and no M33. Broken line indicates mice injected ip with bacteria and a single injection of M33 peptide 10 mg/Kg 30 minutes later. B, Balb-c mice (20 g) were intra-peritoneally injected with a lethal amount of *P. aeruginosa* cells (ATCC 27853 $1 \times 10^7$ CFU). Continuous line (Ctr) indicates mice which only received bacteria; other groups received bacteria and a single dose of M33 30 minutes later (see figure for doses of M33). C, Balb-c mice (20 g) were intra-peritoneally injected with a lethal amount of *P. aeruginosa* cells (multi drug resistant VR 147 clinical isolate, $1.5 \times 10^7$ CFU). Continuous line (Ctr) indicates mice which only received bacteria; broken line indicates mice which received bacteria and a single dose of M33 25 mg/Kg. D, Balb-c mice (20 g) were intra-peritoneally injected with a lethal amount of *P. aeruginosa* cells (ATCC 27853 $1 \times 10^7$ CFU). Continuous line (Ctr) indicates mice which only received bacteria; long broken line, mice receiving bacteria and two injections of M33 (5 mg/Kg×2), 30 minutes and 12 hours after bacteria; short broken line, mice receiving bacteria and three injections of M33 (5 mg/Kg×3), 30 minutes, 12 and 24 hours after bacteria. $P<0.05$.

DETAILED DESCRIPTION OF THE INVENTION

Peptide Synthesis

Monomeric peptide was synthesized as peptide amide by an automated synthesizer (MultiSynTech, Witten, Germany) on a Rink Amide MBHA resin (Nova Biochem) using 9-fluorenylmethoxycarbonyl (Fmoc) chemistry and O-(benzotriazol-1-yl)-N,N,N',N'-tetramethyluronium hexafluorophosphate/1,3-diisopropylethylamine activation. Branched peptide molecules (MAPs) were synthesized on $Fmoc_4$-Lys-Lys-βAla Wang resin. Side chain protecting groups were trityl for Gln, tert-butoxycarbonyl for Lys, 2,2,4,6,7-pentamethyldihydrobenzofuran-5-sulfonyl for Arg, and tert-butyl ether for Ser. Peptides were then cleaved from the resin and deprotected with trifluoroacetic acid containing water and triisopropylsilane (95/2.5/2.5). Crude peptides were purified by reversed-phase chromatography on a Vydac C18 column. Identity and purity of final products was confirmed by Ettan™ MALDI-TOF mass spectrometry (MS) (Amersham Biosciences).

Protease Resistance of Tetra-Branched M33, M34, M35 and M36

A total of 10 μl of a 10 mM solution of peptide was incubated at 37° C. with 10 μl human serum. Samples were collected after 24 h of incubation, precipitated with 150 μl methanol, and centrifuged for 2 min at 10,000×g. The crude solution was then analyzed by high-performance liquid chromatography (HPLC) and MS. HPLC was performed with a Vydac C18 column, and the crude solution was diluted five times with 0.1% trifluoroacetic acid before injection and monitored at 280 nm.

Stability of Peptides M33, M34, M35 and M36

A single colony of *E. coli* TG1 strain was cultured in 2×TY medium to 0.2 $OD^{600}$. 25 μl of peptides diluted as depicted in FIG. 1 and 25 μl of *E. coli* derived from the previous culture were incubated in 96 well plate for 75 minutes at 37° C. in mild agitation. As control we used one well incubated with 25 μl of *E. coli* and 25 μl of medium only (100% viability). After incubation the solution of every well was diluted 1:1000 and plated on a agar 2×TY plate. Plates were incubated over night at 30° C. The following day colonies (CFU/ml) grown on plates were counted.

Different batches of tetra-branched peptide M6 (QKKIRVRLSA, SEQ ID NO. 5) provided dissimilar results against *E. coli* when analyzed in parallel in the same experiment (M6 batch 1, 2 and 3 of FIG. 1A). Tetra-branched M6 was therefore analyzed by mass spectrometry, which revealed two main peaks, one corresponding to the regular molecular mass of M6 and the other to the molecular mass of a tetra-branched peptide containing pyroGlu as first residue (FIG. 1B). Different preparations of M6 obtained by identical procedures gave MS profiles with the two peaks always in different proportions, confirming that conversion of the first Gln into pyroGlu occurred in an unpredictable percentage. The presence of pyroGlu instead of Gln impaired the antimicrobial activity of M6 as demonstrated by a tetra-branched peptide in which the first aminoacid was 100% pyroGlu (pyro-M6 of FIG. 1A). Therefore, peptide M6 can not be considered a real candidate for the development of a new drug.

The elimination of the first aminoacid from peptide M6 sequence (QKKIRVRLSA, SEQ ID NO. 5), and the possible substitution of first two Lys with Arg, or alternating these two aminoacids, produced 4 new sequences (KKIRVRLSA, SEQ ID NO. 1, RRIRVRLSA, SEQ ID NO. 2, KRIRVRLSA, SEQ ID NO. 3, RKIRVRLSA, SEQ ID NO. 4) with a highly stable activity of peptides derived from synthesis carried out in different periods. In particular, the peptide called M33: KKIRVRLSA, SEQ ID NO. 1, was synthesized in many different batches, all of which gave the same MS profile with a single peak corresponding to the molecular mass of the tetra-branched M33 (FIG. 1C). As expected, tetra-branched M33 was also very stable to proteolytic degradation when incubated in serum for 24 h (FIG. 1C). Indeed, elimination of the first residue from the sequence of M6 not only stabilized batch-to-batch homogeneity but also improved peptide anti-bacterial activity (M33 in FIG. 1A).

Many different syntheses of M33, M34, M35 and M36 gave perfectly overlapping results without any fluctuations in outcome.

The above demonstrated stability renders peptides M33, M34, M35 and M36 very appealing candidates for the creation of a new antibacterial medicine.

Antibacterial Activity of Tetra-Branched Peptides M33, M34, M35 and M36

Minimum Inhibitory Concentration (MIC) was determined by a standard microdilution assay as recommended by the National Committee for Clinical Laboratory Standards (NCCLS) using cation-supplemented Mueller-Hinton (MH) broth (Oxoid Ltd. Basingstoke, UK) and a bacterial inoculum of $5 \times 10^4$ CFU per well, in a final volume of 100 Results were recorded by visual inspection after 24 h of incubation at 37° C. M33, M4, M35 and M36 MICs were determined against strains of several bacterial species, including Gram-negative pathogens and also *Staphylococcus aureus* (Table 1). MICs in the micromolar range were observed against several Gram-negatives including *Pseudomonas aeruginosa, Acinetobacter baumannii* and most Enterobacteriaceae, with the exception of *Proteus mirabilis, Serratia marcescens* and *Burkholderia cepacia*. Activity of peptides was retained against MDR strains with various resistance mechanisms (such as extended-spectrum beta-lactamases and carbapenemases), including MDR *P. aeruginosa* strains from CF patients. Antimicrobial profile of M33, M4, M5 and M6 and potency were overall similar to those of polymyxin B, although M33, M34, M35 and M36 also appeared to have some activity against *S. aureus* (Table 1).

TABLE 1

MICs (μM) of M33 in comparison with polymyxin B against bacterial strains representative of several pathogenic species, including MDR strains of clinical origin

| Species and strains | Relevant features[a] | M33 | M34 | M35 | M36 | Polymyxin B |
|---|---|---|---|---|---|---|
| *Pseudomonas aeruginosa* ATCC 27853 | Reference strain, wild type | 1.5 | 1.5 | 1.5 | 1.5 | 1.5 |
| *P. aeruginosa* PAO-1 | Reference strain, wild type | 1.5 | 1.5 | 1.5 | 1.5 | 1.5 |
| *P. aeruginosa* VR-143/97 | FQ[r] AG[r] ESC[r] NEM[r] (MBL/VIM-1) | 1.5 | 1.5 | 1.5 | 1.5 | 1.5 |
| *P. aeruginosa* AV65 | FQ[r] AG[r] ESC[r] NEM[r] (MBL/IMP-13) | 1.5 | 1.5 | 1.5 | 1.5 | 1.5 |
| *P. aeruginosa* SC-MDr03-06[b] | FQ[r] AG[r] ESC[r] NEM[r] | 3 | 3 | 3 | 3 | 1.5 |
| *P. aeruginosa* SC-VMr04-05[b] | FQ[r] AG[r] ESC[r] NEM[r] | 3 | 3 | 3 | 3 | 1.5 |
| *P. aeruginosa* SC-DMr05-04[b] | FQ[r] AG[r] ESC[r] NEM[r] | 1.5 | 1.5 | 1.5 | 1.5 | 1.5 |
| *P. aeruginosa* SC-BGr12-02[b] | FQ[r] AG[r] ESC[r] NEM[r] | 1.5 | 1.5 | 1.5 | 1.5 | 1.5 |
| *P. aeruginosa* EF-OBG6-1[b] | FQ[r] AG[r] ESC[r] NEM[r] (MBL/IMP-13) | 0.7 | 1.5 | 1.5 | 1.5 | 0.7 |
| *P. aeruginosa* SC-MDm03-02[b,c] | FQ[r] AG[r] ESC[r] NEM[r] | 3 | 3 | 3 | 3 | 1.5 |
| *P. aeruginosa* SC-GMm03-05[b,c] | FQ[r] AG[r] ESC[r] NEM[r] | 1.5 | 1.5 | 1.5 | 1.5 | 1.5 |
| *P. aeruginosa* SC-CNm03-07[b,c] | FQ[r] AG[r] ESC[r] NEM[r] | 0.3 | 1.5 | 1.5 | 0.3 | 0.7 |
| *Klebsiella pneumoniae* ATCC 13833 | Reference strain, wild type | 1.5 | 1.5 | 3 | 1.5 | 0.7 |
| *K pneumoniae* 7086042 | FQ[r] AG[r] ESC[r] NEM[r] (MBL/VIM-1) | 3 | 3 | 3 | 3 | 1.5 |
| *K pneumoniae* C8-27 | FQ[r] AG[r] ESC[r] ETP[r] (ESBL/CTX-M-15) | 1.5 | 1.5 | 1.5 | 1.5 | 0.7 |
| *K pneumoniae* FIPP-1 | FQ[r] AG[r] ESC[r] NEM[r] (MBL/KPC-3) | 3 | 3 | 3 | 3 | 1.5 |
| *Escherichia coli* ATCC 25922 | Reference strain, wild type | 1.5 | 1.5 | 1.5 | 1.5 | 0.7 |
| *E. coli* W03BG0025 | FQ[r] AG[r] ESC[r] (ESBL/CTX-M-15) | 0.7 | 1.5 | 1.5 | 1.5 | 0.7 |
| *E. coli* W03AN0048 | | | | | | |
| *Proteus mirabilis* W03VA1017 | FQ[r] ESC[r] (AmpC/CMY-16) | >24 | >24 | >24 | >24 | >96 |
| *Enterobacer aerogenes* W03BG0067 | AG[r] ESC[r] (ESBL/SHV-5) | 1.5 | 1.5 | 1.5 | 1.5 | 0.7 |
| *Enterobacter cloacae* W03AN0041 | ESC[r] (ESBL/SHV-12) | 1.5 | 3 | 1.5 | 3 | 0.7 |
| *Acinetobacter baumannii* RUH 134 | Reference strain, European clone II | 1.5 | 1.5 | 1.5 | 1.5 | 1.5 |
| *A. baumannii* RUH 875 | Reference strain, European clone I | 3 | 3 | 3 | 3 | 1.5 |
| *A. baumannii* MR157 | FQ[r] AG[r] ESC[r] NEM[r] (OXA/OXA-58) | 3 | 3 | 3 | 3 | 1.5 |
| *Burkholderia cepacia* ORB-99[b] | Wild type | >24 | >24 | >24 | >24 | >96 |
| *Serratia marcescens* W03BG0003 | FQ[r] AG[r] ESC[r] (ESBL/SHV-12) | >24 | >24 | >24 | >24 | >96 |

TABLE 1-continued

MICs (μM) of M33 in comparison with polymyxin B against bacterial strains
representative of several pathogenic species, including MDR strains of clinical origin

| Species and strains | Relevant features[a] | M33 | M34 | M35 | M36 | Polymyxin B |
|---|---|---|---|---|---|---|
| Staphylococcus aureus ATCC 29213 | Reference strain, PEN[r] | 6 | 6 | 6 | 6 | 96 |
| S. aureus 3851 | MR VAN[i] | 6 | 6 | 6 | 6 | 96 |

[a] Tested strains included either reference strains (indicated) or clinical isolates (mostly showing an MDR phenotype); relevant resistance traits and resistance mechanisms are indicated:_FQ[r], resistant to fluoroquinolones; AG[r], resistant to aminoglycosides (gentamicin, amikacin, and/or tobramycin); ESC[r], resistant to expanded-spectrum cephalosporins; NEM[r], resistance to carbapenems (imipenem and/or meropenem), ERT[r] resistance to ertapenem; COL[NS], nonsusceptible to colistin; ESBL, extended spectrum β- lactamase; MBL, metallo-β-lactamase; OXA, oxacillinase; MR methicillin-resistant; VAN[i], vancomycin-intermediate
[b] Clinical isolates from Cystic Fibrosis patients
[c] Mucoid phenotype Peptides described in the present invention appeared particularly selective for Gram negative bacteria, probably because they bind strongly to LPS, which is constitutively present in Gram negative bacteria only. The amphypatic profile, and the large excess of positive charges of the peptides, suggests also that they might interact with bacterial membranes entering the cells by one of the mechanisms of action described for antimicrobial peptides with similar structure.

Haemolytic Activity of Tetra-Branched Peptides M33, M34, M35 and M36

Haemolysis of fresh human erythrocytes was determined using the method of Parpart, summarized as follows. A calibration curve was constructed by suspending fresh human erythrocytes in phosphate buffer (pH 7.4, 110 mM sodium phosphate) with various concentrations of NaCl and incubated for 30 min at room temperature. Samples were centrifuged at 500×g for 5 minutes, and haemoglobin release was monitored by measuring the absorbance of supernatants at 540 nm. The absorbance obtained with 0.1% NaCl corresponded to 100% lysis and that with 1% NaCl, to 0% lysis. Peptides dissolved in PBS were added to human erythrocyte solution at several concentrations. The resulting suspension was incubated separately at 37° C. for 2 h and 24 h. Release of hemoglobin was monitored by measuring the absorbance of the suspernatant at 540 nm after centrifuging and haemolysis percentage was calculated using the calibration curve.

A very important feature is that, contrary to most antimicrobial peptides described so far, M33, M34, M35 and M36 peptides show a practically negligible haemolysis grade (FIG. 2), suggesting their possible use also through systemic administrations.

Neutralization of Lypopolysaccaride (LPS)

In Gram-negative bacterial infections, release of LPS is known to be involved in the pathophysiology of sepsis and septic shock. Antimicrobial peptides that also effectively neutralize LPS are of considerable importance in combating sepsis.

Initially, tetra-branched M33 was analysed in a *Limulus amebocyte* lysate test (E-toxate) demonstrating its ability to neutralize sample gelification due to LPS (not shown). Then it was examined for inhibiting LPS-induced TNF-α, secretion by Raw 264.7 macrophages. M33 resulted able to block TNF-α, secretion in a dose-dependent manner when macrophages were stimulated with LPS from *P. aeruginosa* serotype 10 ATCC27316 (FIG. 3A), and *K. pneumoniae* ATCC15380 (FIG. 3B) with an EC50 of 4e-8 M and 2.6e-7 M, respectively. Notably, at a concentration corresponding to MIC (between 1.5 and 3 μM for *P. aeruginosa* and *K. pneumoniae*), M33 decreased TNF-α, production by more than 90% when macrophages were stimulated with LPS from *P. aeruginosa* and by more than 80% when stimulated with LPS from *K. pneumoniae*. M33 only stimulated a quantifiable amount of TNF-α when incubated with macrophages at three time MIC concentration.

In Vivo Antibacterial Activity

Tetra-branched M33 peptide was analysed for its antibacterial activity in mice infected with lethal amounts of bacteria. Two different bacterial species were used, *Escherichia coli* and *Pseudomonas aeruginosa*. The smallest number of bacteria causing 100% lethal infection (LD100) after intra-peritoneal (ip) injection was $1.5 \times 10^9$, $1 \times 10^7$ and $1.5 \times 10^7$ for *E. coli* TG1, *P. aeruginosa* ATCC 27853 and the MDR clinical isolate *P. aeruginosa* VR143/97, respectively. Bacterial LD100 killed mice in 20-24 hours. Balb-c mice were infected with the LD100 of bacteria and treated 30 minutes later with the peptide by ip administration.

Following infection with *E. coli* TG1, M33 protected 100% of animals from signs of sepsis and death (seven-day survival) when administered in a single dose at a concentration of 10 mg/Kg (FIG. 4A). After the mice were challenged with *P. aeruginosa* ATCC 27853, M33 administered in a single dose at the concentrations of 25 mg/Kg and 12.5 mg/Kg protected 75% and 25% of animals, while at 6.5 mg/Kg it did not protect them from death, although death was delayed in comparison with untreated controls (FIG. 4B). Finally, *P. aeruginosa* VR-143/97, an MDR strain susceptible only to polymyxin B (19) and representative of a clone currently spreading in Italy (Cornaglia et al., 2000), was used to challenge mice. M33 administered in a single dose at the concentrations of 25 mg/Kg protected 100% of animals (FIG. 4C). M33 was then analyzed for its activity when administered in multiple doses following infection with *P. aeruginosa* ATCC 27853. When mice were treated with two doses of 5 mg/Kg M33 every twelve hours (30 min and 12 h after infection) death was delayed. When mice were treated with three doses of 5 mg/Kg M33 every twelve hours (30 min, 12 h and 24 h after infection) full protection from signs of sepsis was obtained and 100% survived beyond seven days after infection (FIG. 4D).

M33 did not produce apparent toxicity signs in animals treated ip with a peptide dose of 100 mg/Kg (not shown), 4 time the dose reported in this article.

Antimicrobial activity of M33 in vivo was also evaluated by counting bacteria at different times in blood, peritoneal fluid, spleen and liver after infection with LD100 of *P. aeruginosa* ATCC 27853 and treatment with a single dose of M33 at 25 mg/Kg. 18 h after infection, blood was apparently clear of bacteria and bacterial counts in peritoneal fluid, spleen and liver were significantly lower than in controls. After 40 hours, all sampled body sites were apparently clear of bacteria (Table 2).

TABLE 2

Efficacy of M33 in reducing bacterial load of *P. aeruginosa* in a mouse sepsis model

| Groups of animals (5 mice/group) | Bacterial count (mean ± SD) in: | | | |
|---|---|---|---|---|
| | Blood (CFU/ml) | Peritoneum (CFU/ml) | Spleen (CFU/organ) | Liver (CFU/organ) |
| Control group[a] | $7.6 \times 10^3 \pm 1.6 \times 10^3$ | $3.6 \times 10^6 \pm 1.9 \times 10^6$ | $3.5 \times 10^6 \pm 5.1 \times 10^6$ | $1.2 \times 10^7 \pm 1.4 \times 10^7$ |
| M33 group 18 hours[b] | $<1 \times 10^2$ | $1.4 \times 10^4 \pm 3.1\ 10^4$ | $2.4 \times 10^4 \pm 5.3 \times 10^4$ | $3 \times 10^5 \pm 6.7 \times 10^5$ |
| M33 group 40 hours[c] | $<1 \times 10^2$ | $<1 \times 10^2$ | $<1 \times 10^2$ | $<1 \times 10^2$ |

[a] Moribund animals (sacrificed 18 h after infection) injected ip with *P. aeruginosa* $1 \times 10^7$ CFU/mouse
[b] Animals injected ip with *P. aeruginosa* $1 \times 10^7$ CFU/mouse, treated with M33 (25 mg/Kg) and sacrificed 18 h after infection
[c] Animals injected ip with *P. aeruginosa* $1 \times 10^7$ CFU/mouse, treated with M33 (25 mg/Kg) and sacrificed 40 h after infection

BIBLIOGRAPHY

Bracci L, et al., 2003, J Biol Chem, 278: 46590-5
Cornaglia G, et al., 2000, Clin Infect Dis, 31: 1119-25
Falciani C, et al., 2007, Chem Biol Drug Des, 69: 216-21
Hancock R E and Sahl H G, 2006, Nat Biotecnol 24: 1551-7
Pini A, et al., 2005, Antimicrob Agents Chemother, 49: 2665-72
Pini A, et al, 2007, J Pept Sci, 13: 393-9
Wenzel R P and. Edmond M B, 2000, N Engl J Med 343: 1961-3
Zasloff M. 2002, Nature, 415:389-95

The invention claimed is:

1. An antibacterial peptide consisting from the amino to the carboxylic terminal of an amino acid sequence selected from the group consisting of: KKIRVRLSA (SEQ ID NO. 1), RRIRVRLSA (SEQ ID NO. 2), KRIRVRLSA (SEQ ID NO. 3), and RKIRVRLSA (SEQ ID NO. 4).

2. The peptide according to claim 1 being of linear form.

3. The peptide according to claim 2, multimerised on a skeleton of polyacrylamide, on a skeleton of dextrane units or on a skeleton of ethylene glycol units.

4. The peptide according to claim 1, being in the form of Multiple Antigenic Peptides (MAP), having the following formula:

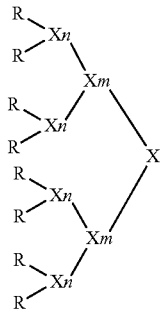

in which R is the peptide as claimed in claim 1; X is a trifunctional molecule; m=0 or 1; n=0 or 1; when m and n are 0 the peptide is a dimer; when m=1 and n=0 the peptide is a tetramer; when m=1 and n=1 the peptide is an octamer.

5. The MAP peptide according to claim 4, wherein X is a trifunctional unit.

6. The MAP peptide according to claim 5, wherein the trifunctional unit comprises at least two functional aminic groups.

7. The MAP peptide according to claim 6, wherein X is lysine, ornithine, nor-lysine or amino alanine.

8. The MAP peptide according to claim 4, wherein X is aspartic acid or glutamic acid.

9. The MAP peptide according to claim 4, wherein X is propylene glycol, succinic acid, diisocyanates or diamines.

10. A method of treating bacterial infection in a subject in need thereof comprising,
   administering to a subject suffering from a bacterial infection an effective amount of the peptide according to claim 1, and
   treating said subject.

11. A pharmaceutical composition comprising a pharmaceutically acceptable and effective quantity of the peptide according to claim 1.

12. The pharmaceutical composition according to claim 11, in the form of a solution to be injected in individuals for systemic use.

13. A method for neutralizing lipopolysaccharides in a subject in need thereof comprising
   injecting an effective amount of a solution comprising the pharmaceutical composition according to claim 11 to a subject in need thereof.

14. The pharmaceutical composition according to claim 11, in the form of eyewash, mouth wash, ointment, or solution for topic use.

15. A disinfectant or detergent preparation with antibacterial activity comprising the peptide according to claim 1.

16. The method of claim 10, comprising administering 25 mg/Kg in a single dose.

17. The method of claim 10, comprising administering 10 mg/Kg in a single dose.

18. The method of claim 10, comprising administering three doses of 5 mg/Kg every 12 hours.

* * * * *